United States Patent [19]

Patel

[11] Patent Number: 4,705,502
[45] Date of Patent: Nov. 10, 1987

[54] SUPRAPUBIC CATHETER WITH DUAL BALLOONS

[75] Inventor: Bhupendra C. Patel, Elgin, Ill.

[73] Assignee: The Kendall Company, Boston, Mass.

[21] Appl. No.: 948,186

[22] Filed: Dec. 31, 1986

Related U.S. Application Data

[60] Continuation of Ser. No. 795,308, Nov. 6, 1985, abandoned, which is a division of Ser. No. 651,371, Sep. 17, 1984, abandoned.

[51] Int. Cl.$^4$ ............................................. A61M 25/00
[52] U.S. Cl. ........................................ 604/49; 604/101
[58] Field of Search ................... 604/101, 51, 49, 54, 604/55; 128/344

[56] References Cited

U.S. PATENT DOCUMENTS

| | | | |
|---|---|---|---|
| 3,680,562 | 8/1972 | Wittes et al. | 604/51 |
| 3,961,632 | 6/1976 | Moosun | 604/51 |
| 4,022,216 | 5/1977 | Stevens | 604/101 |

FOREIGN PATENT DOCUMENTS 840947  2/1959  United Kingdom ............... 604/101

Primary Examiner—Stephen C. Pellegrino
Attorney, Agent, or Firm—Powell L. Sprunger

[57] ABSTRACT

A suprapubic catheter comprising, an elongated shaft having a drainage lumen extending therethrough, and a plurality of openings extending through the shaft and communicating with the drainage lumen. The catheter has a first elastic sleeve secured to the shaft in spaced circumferential zones and defining a first cavity beneath the first sleeve, with the first sleeve being located adjacent a distal end of the shaft. The catheter has a second elastic sleeve secured to the shaft in spaced circumferential zones and defining a second cavity beneath the second sleeve, with the second sleeve being located proximal the first sleeve, and with the openings being located intermediate the first and second sleeves. The catheter has one or more inflation lumens extending along the shaft for inflating the first and second sleeves.

1 Claim, 2 Drawing Figures

SUPRAPUBIC CATHETER WITH DUAL BALLOONS

This is a continuation of application Ser. No. 795,308, filed Nov. 6, 1985, a divisional of Ser. No. 651,371, filed Sept. 17, 1984 both abandoned.

BACKGROUND OF THE INVENTION

The present invention relates to suprapubic catheters.

Patients are commonly catheterized with urinary or Foley catheters in which the catheter is passed through the urethra of a patient until a distal end of the catheter is located in the patient's bladder. During catheterization with a urinary catheter, urine drains from the bladder through the catheter, and through a drainage tube attached to a promixal end of the catheter to a drainage bag for collection therein. In suprapubic systems, a catheter is passed through the abdominal wall of the patient until a distal end of the catheter is located in the bladder. During catheterization with a suprapubic catheter, urine drains from the bladder through the catheter, through a drainage tube connected to a proximal end of the catheter to a drainage bag for collection therein.

There are important advantages of the suprapubic catheter over the urinary catheter. First, the incidence of infection in the suprapubic systems is much less than that in urinary catheters. Second, if surgery has taken place in the region of the urethra, it is desirable to keep the catheter from the surgical area to promote healing. Third, urinary catheters prevent normal voiding by the patient, while the suprapubic systems permit voiding once the drainage tube in the suprapubic system is closed. Hence, in suprapubic systems the physician may readily determine whether the patient is ready to void naturally, while in urinary catheter systems the catheter must be removed from the patient to achieve this result. Finally, the suprapubic systems are more comfortable for the patient than urinary catheters, and the suprapubic systems increase the mobility of the patient.

However, prior suprapubic catheters generally have a coil at a distal end located in the bladder, and it has been found that some of the coils of thermoplastic materials have a tendency to straighten out and pass into the urethra thus blocking drainage of the catheter.

SUMMARY OF THE INVENTION

A principal feature of the present invention is the provision of an improved suprapubic catheter.

The suprapubic catheter of the present invention comprises, an elongated shaft having a drainage lumen extending therethrough, and a plurality of openings extending through the shaft and communicating with the drainage lumen. The catheter has a first elastic sleeve secured to the shaft in spaced circumferential zones and defining a first cavity beneath the first sleeve, with the first sleeve being located adjacent a distal end of the shaft. The catheter has a second elastic sleeve secured to the shaft in spaced circumferential zones and defining a second cavity beneath the second sleeve, with the second sleeve being located proximal the first sleeve, and with the openings being located intermediate the first and second sleeves. The catheter has means for inflating the first and second sleeves.

A feature of the present invention is that the inflated second sleeve retains the catheter in place in the bladder, and prevents accidental pull out of the catheter from the bladder.

Still another feature of the invention is that the inflated second sleeve seals against the bladder and prevents leakage around the catheter.

Yet another feature of the invention is that the inflated second sleeve indicates how far the catheter should be pulled out with the distal portion of the catheter in place in the bladder.

A further feature of the invention is that the inflated first sleeve prevents the catheter from passing into the urethra.

Thus, a feature of the invention is that the inflated first sleeve prevents blockage of the catheter.

Further features will become more fully apparent in the following description of the embodiments of this invention and from the appended claims.

DESCRIPTION OF THE PREFERRED EMBODIMENTS

Figure 1:
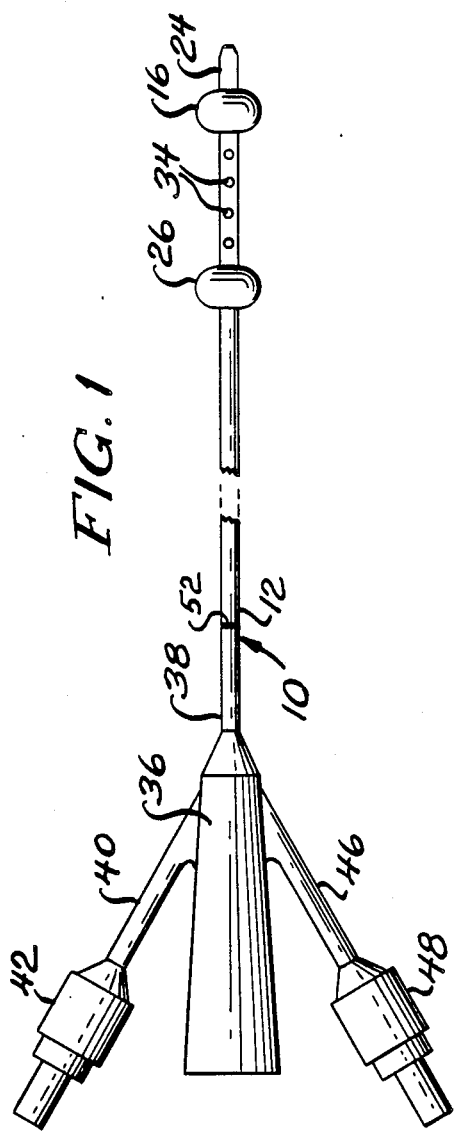
FIG. 1 is a fragmentary elevational view of a suprapubic catheter of the present invention.
Figure 2:
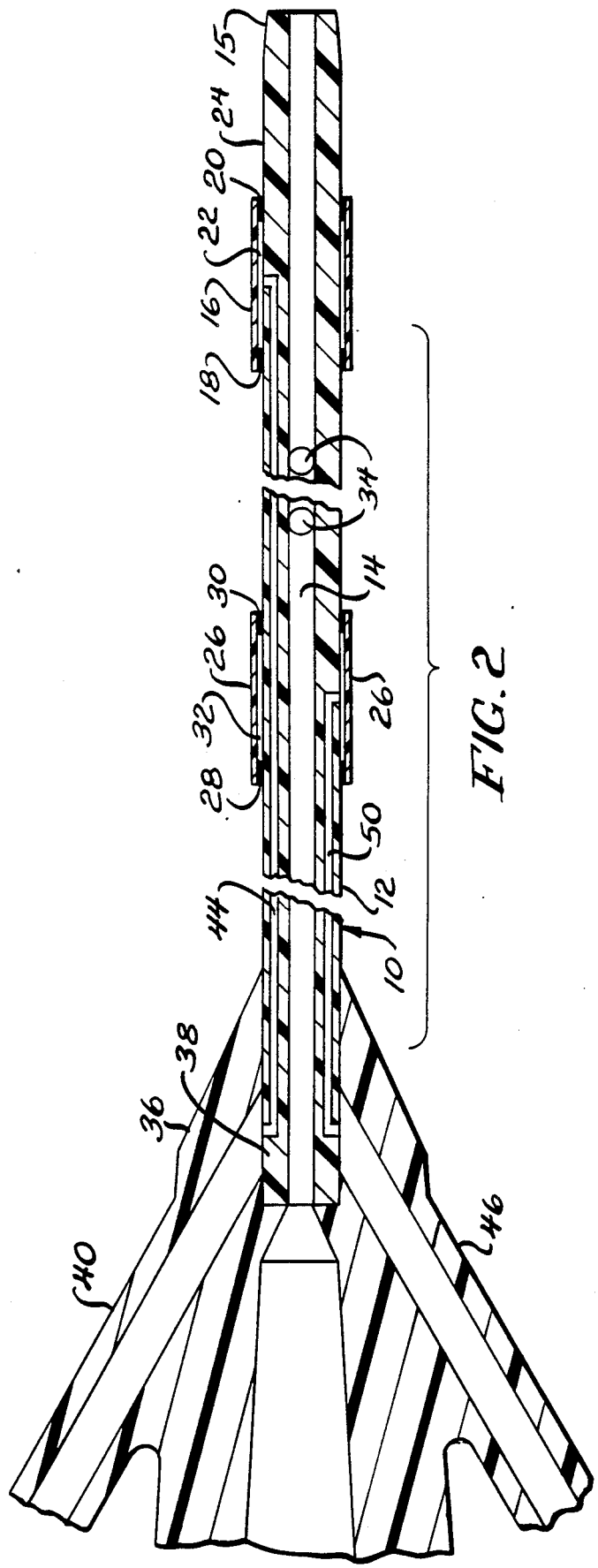
FIG. 2 is a fragmentary sectional view of the catheter of FIG. 1.

Referring now to FIGS. 1 and 2, there is shown a suprapubic catheter generally designated 10 having an elongated shaft 12, with the shaft 12 having a drainage lumen 14 extending therethrough. The shaft 12 may have an open distal end 15.

The catheter 10 has a first elastic sleeve or balloon 16 bonded to the shaft 12 in spaced circumferential zones 18 and 20 at ends of the first sleeve 16, with the first sleeve 16 defining a first cavity 22 beneath the first sleeve 16. As shown, the first sleeve 16 is located adjacent a distal end portion 24 of the shaft 12.

The catheter 10 has a second elastic sleeve or balloon 26 secured to the shaft 12 in spaced circumferential zones 28 and 30 at ends of the second sleeve 26, with the second sleeve 26 defining a second cavity 32 beneath the second sleeve 26. As shown, the second sleeve 26 is located proximal the first sleeve 16. The shaft 12 has a plurality of openings 34 extending through the shaft 12 and communicating with the drainage lumen 14 at a location intermediate the first and second sleeves 16 and 26.

The catheter 10 has a connector 36 attached to a proximal end 38 of the shaft 12. The connector 36 has a first side arm 40 having a first valve 42 of known type which actuates by contact of the tip of a syringe (not shown). The first side arm 40 and shaft 12 have a first inflation lumen 44 communicating between the first valve 42 and the first cavity 22 of the first sleeve 16.

The connector 36 has a second side arm 46 having a second valve 48 of known type which actuates by contact of a tip of a syringe. The second side arm 46 and shaft 12 have a second inflation lumen 50 extending between the second valve 48 and the second cavity 32. The catheter 10 may be constructed from silicon.

In use, a puncture is made in the abdominal wall of the patient, and the catheter 10 is passed through the puncture until the first and second balloons 16 and 26 are located in the bladder of the patient. A depth mark 52 is provided on the shaft 12 to indicate when the balloons are in the bladder. Next, the first balloon 16 is inflated by contacting the first valve 42 with the syringe and pumping fluid through the first valve and first inflation lumen 44 into the first cavity 22. The second balloon 26 is then inflated by contacting the second valve 48 with the syringe and pumping fluid through the second valve 48 and second inflation lumen 50 into the second cavity 32. The catheter 10 is then pulled proximally until the second inflated balloon 26 contacts the bladder wall.

Thus, the inflated second balloon retains the catheter in place in the bladder, and prevents accidental pulling out of the catheter from the bladder. Also, the inflated second balloon seals against the bladder and prevents leakage around the catheter, and also indicates how far the catheter should be pulled out with the first balloon 16 in place in the bladder. The inflated first balloon 16 prevents the catheter from passing into the urethra, and thus prevents possible blockage of the catheter 10.

The foregoing detailed description is given for clearness of understanding only, and no unnecessary limitations should be understood therefrom, as modifications will be obvious to those skilled in the art.

I claim:

1. A method of performing a suprapubic procedure comprising the steps of:
    passing the shaft of a catheter through the abdominal wall of a patient's body until a distal portion of the shaft containing a first distal sleeve and a second proximal sleeve is located in the patient's bladder;
    inflating the first and second sleeves in the bladder with the inflated first sleeve preventing passage of the shaft into the urethra; and
    pulling the shaft proximally until the inflated second sleeve seals against the bladder to prevent leakage around the shaft.

* * * * *